United States Patent
Wunderlich et al.

(10) Patent No.: US 6,468,959 B1
(45) Date of Patent: *Oct. 22, 2002

(54) PERORAL DOSAGE FORM FOR PEPTIDE CONTAINING MEDICAMENTS, IN PARTICULAR INSULIN

(75) Inventors: Jens-Christian Wunderlich, Heidelberg; Ursula Schick, Wiesloch; Jurgen Freidenreich, Schriesheim; Jurgen Werry, Ludwigshafen, all of (DE)

(73) Assignee: ALFATEC-Pharm GmbH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/222,714

(22) Filed: Apr. 5, 1994

Related U.S. Application Data

(63) Continuation-in-part of application No. 07/876,867, filed on Apr. 30, 1992, now abandoned.

(30) Foreign Application Priority Data

Dec. 5, 1991 (DE) .......................... 41 10 186

(51) Int. Cl.$^7$ .................................. A61K 9/24
(52) U.S. Cl. ............... 514/2; 514/3; 514/773; 514/774; 424/472; 424/464; 424/465; 424/468; 424/469; 424/474; 424/484
(58) Field of Search .................... 424/464, 465, 424/468, 469, 472, 474–480, 484; 514/2, 3, 773, 774

(56) References Cited

U.S. PATENT DOCUMENTS

| | | | | |
|---|---|---|---|---|
| 4,608,278 A | * | 8/1986 | Frank | 427/213.35 |
| 4,761,407 A | * | 8/1988 | Campan | 514/179 |
| 4,774,091 A | * | 9/1988 | Yamahira | 424/426 |
| 4,800,191 A | * | 1/1989 | Schally | 514/15 |
| 4,816,568 A | * | 3/1989 | Hamilton | 530/399 |
| 4,935,243 A | * | 6/1990 | Borkan | 424/441 |
| 5,494,898 A | * | 2/1996 | Cheng | 514/18 |
| 5,614,219 A | * | 3/1997 | Wunderlich | 424/472 |

OTHER PUBLICATIONS

Burgess, International Journal of Pharmaceutics 32, 207, 1986.*

Gennaro, Remington's Pharmaceutical Sciences, 18$^{th}$ Ed., (1990), pp. 291–293 and 1682–1684.*

* cited by examiner

*Primary Examiner*—Christopher S. F. Low
*Assistant Examiner*—David Lukton
(74) *Attorney, Agent, or Firm*—Selitto, Behr & Kim

(57) ABSTRACT

There is provided a plural dosage form for peptide pharmaceuticals comprising a matrix of gelatin or gelatin derivative having distributed therein the peptide pharmaceutical in particular insulin, as well as, pharmaceutically conventional carriers and additives. By selection of the appropriate gelatin the pharmaceutical is liberated in the small intestine or the large intestine so that is not enzymatically degraded anymore by peptidases.

10 Claims, No Drawings

PERORAL DOSAGE FORM FOR PEPTIDE CONTAINING MEDICAMENTS, IN PARTICULAR INSULIN

This application is a continuation, of application Ser. No. 07/876,867, filed Apr. 30, 1992 now abandoned.

FIELD OF THE INVENTION

The invention concerns a peroral application form for peptide pharmaceuticals, wherein at least one peptide pharmaceutical is distributed in a matrix of gelatin or a gelatin derivative together with pharmaceutically conventional carriers and inactive ingredients. The invention further concerns a process for the preparation of such peroral dosage forms.

BACKGROUND OF THE INVENTION

In highly industrial countries, it may be assumed that from about 2 to about 3% of the population exhibit the symptoms of diabetes. For the effective handling of this disease with its most important symptoms such as hypoglycemia, hyperuresis, glucouria, as well as hypolipidemia, despite enormous and varied pharmaceutical developments, the exogenous administration of insulin is still the mainstay of treatment. Even the orally administrable antidiabetics of the sulfonyl urea type which are only then indicated when the patient's production of insulin is still partially maintained, yield only a limited field of use.

The most substantial administration of insulin is by injection (parenteval application). Other modes of application, for example, nasal, pulmonal, rectal, and especially peroral, are presently under investigation.

At the present time, it is not apparent that an appropriate product has been able to achieve an adequate level of market acceptability. Rather one can say that these alternate modes are in the stage of orientation research. It is well known that injections carry disadvantages. Thus, at the point of application for example, lipodystrophy or other foreign body reactions may occur, Problems with the handling of syringes are particularly to be expected with very young and old patients. A regularly available injection with patient groups must often be undertaken by a trusted person. It is clear that this requirement does not exactly assist in patient compliance.

The optimal, simplest and surest mode of use of pharmaceuticals in contrast, is the peroral application. For example with tablets, capsules, and potable solutions. In the case of peptide pharmaceuticals for example insulin, substantial difficulties arise since these are already inactivated through enzymatic degradation to a substantial extent when released in the gastrointestinal tract (GIT; stomach or small intestine) before absorption. The enzymatic degradation in the gastric or small intestinal fluid, or on the mucosa threatens to reduce the bioavailability of peptide materials in particular, insulin to a minimum. Furthermore, the absorption mechanism for peptide pharmaceuticals by passive transport is substantially unavailable. This is due, on the one hand, to the molecular size, which for passive transport has a limit of about 500 daltons. On the other hand, substance specific properties such as hydrophilicity (lower distribution co-efficient), self association to larger entities, or binding to the components of the gastrointestinal tract interfere with absorption. Furthermore, absorption becomes additionally more difficult when the dissociation of functionally active groups results in a negative charge which leads to electrostatic repulsion at the glycocalise whose negatively charged glycoprotein layer covers the lipid double layer. Absorption of peptide pharmaceuticals is nevertheless, of extraordinary importance if one wishes to successfully avoid parenteral administration.

It has already been suggested to administer insulin encapsulated in liposomes. In these researches however, it appeared nevertheless not to have been possible to determine the absorbed insulin amounts quantitatively. Thus, these researches can only give a rough orientation values. The use of liposomes furthermore, carries with it substantial difficulties both in the production and in the storage of the corresponding pharmaceutical forms.

Recently there have been reports about practical arrangements to facilitate the peroral application of insulin. Particularly of interest are pharmaceutical embodiments which are stomach and small intestine resistant and release the insulin only after reaching the peptidase poor colon.

It has similarly been suggested that insulin should be combined with an absorption accelerator in a soft gelatin capsule (EP application 0225 189) wherein the capsule is provided with a coating which first dissolves in the colon and that the insulin is then released together with the aforementioned absorption accelerator. The addition of a absorption accelerator (for example, certain tensides such as salacyl acid derivatives) in the gastrointestinal tract, nevertheless appears to have limited effectiveness since in view of the substantial dilution occurring there. For this reason a very substantial administered amounts which can reach 50% of the capsule content, can already call forth deleterious side effects. Furthermore, the toxic side effects of tensides particularly on the mucous membrane are well known. Thus substantial questions may be raised with respect to the desirability of employing salicylic acid derivatives as pharmaceutically inactive ingredients.

U.S. Pat. No. 4,849,405 suggests embedding insulin in a fluid, aqueous two phase system in a coaszervate system. The behavior of coaszervates are known to create problems in their production. It is not possible to provide an exact control of the process parameters. The reproduceability of the process must therefore be brought into question. In these coaszervates, the embedded insulin should provide a rapidly releasable dosage form wherein the preparation is provided in liquid (emulsion) form. The shelf stability of this system may be considered to be subject to substantial problems. By heat treatment (hardening) or cross-linking with aldehydes (for example glutaraldehyde), together with the subsequent removal of the microcapsules through filtration and drying, the coaszervate may be converted into a shelf stable, but nevertheless more slowly released pharmaceutically active form. In these procedures however, an activity lost of the insulin through chemical change cannot be excluded. It is known that insulin is not only sensitive with respect to heat, but also that it can hardly be expected to remain inert with respect to aldehydes. Furthermore, generally speaking in the process disclosed in U.S. Pat. No. 4,849,405 a substantial insulin loss during the encapsulation process must be reckoned with, which clearly reflects negatively upon the production costs. There is no report on the yield of encapsulated insulin.

The task of the present invention therefore is to provide a dosasge form suitable for the peroral administration of peptide pharmaceuticals in particular, insulin which avoids the problems described in the state of the art and thus, permit secure and effective treatment.

SUMMARY OF THE INVENTION

The problem of the present invention is solved thereby that a pharmaceutically active material namely a peptide pharmaceutical material, in particular insulin is dissolved in a gelatin matrix together with conventional pharmaceutical carriers and inactive ingredients.. Furthermore, this task is solved thereby that the peptide pharmaceutically active material in particular insulin, is associated as a charged molecule by absorptive charge compensation (pseudo coaszervate) with an oppositely charged gelatin. Finally, the task is also solved by absorptive charge compensation (pseudo coaszervate) on a contrary charged gelatin associated system, of a peptide pharmaceutical in particular, insulin for the formation of the dosage form, which leads to a safe and effective treatment of the symptoms of diabetes.

In particular, the present invention makes available a peroral dosage form for peptide pharmaceuticals comprising at least one peptide pharmaceutical in a matrix which, besides the usual pharmaceutical carriers and inactive ingredients, contain at least one hydrophilic molecule selected from the group consisting of gelatin, fractionated gelatin, collagen hydrolysates, gelatin derivatives, as well as mixtures thereof.

Furthermore, the present invention among other things, enables a process for the preparation of a peroral dosage form for peptide pharmaceuticals wherein at least one hydrophilic molecule is chosen from the group consisting of gelatin, fractionated gelatin, collagen hydrolysate, gelatin derivatives, as well as mixtures thereof,one mixed with a peptide pharmaceutical to provide a powder formed macromolecule/pharmaceutical mixture followed by compression of the mixture.

Furthermore, the present invention enables the production of a slowly dissolving peroral dosage form for peptide pharmaceuticals characterized thereby that
a) a hydrophilic molecule is chosen from the group consisting of gelatin, fractionated gelatin, gelatin derviates, as well as mixtures thereof, having a maximum molecular weight distribution in the range of about $9.5 \times 10^4$ through $10^6 D$,
b) the hydrophilic macromolecule is converted into an aqueous sol at a temperature below that of the inactivation temperature of the peptide,
c) the pH value of the sol should lie between that of the IEP of the hydrophilic macromolecule and that of the peptide,
d) the peptide is provided to the macromolecular sol in dissolved or undissolved form,
e) the water is removed and
f) the thus obtained powder is compressed into the dosage form in the usual manner.

In accordance with the present invention, there are provided firstly a peroral dosage form for peptide pharmaceuticals which are producible and useable in the field. An advantage exists therein that the release system of the present invention is suited not only for rapid release but also for delayed release or a combination of rapid release and delayed release. Furthermore, the present invention is the first to significantly raise the absorption quotient of peptide pharmaceuticals in particular insulin, in the gastrointestinal tract.

Further embodiments are disclosed in the following list of parallel U.S. applications. The content of these parallel applications, which are incorporated by reference, were filed contemporaneously herewith at the U.S. Patent and Trademark Office by the same inventors and applicants.

File No. of the German associate attorney P/61AL1717US, Title: "Aloe Vera Juice Containing Pellets for Production Thereof and the Use Thereof as Pharmaceutical Cosmetic and Peroral Agents", U.S. Ser. No. 07/876, 876.

File No. of the German associate attorney P/16AL2718/ US, Title: "Pellets Containing Peptides, Method of Making Same and Use Thereof", U.S. Ser. No. 07/876,865.

File No. of the German associate attorney P/61AL2719/ US, Title: "Means for Containing Active Substances Having a Shell of Hydrophilic Macromolecules, Active Substances and Process for Preparation Thereof", U.S. Ser.No. 07/876, 864.

File No. of the German associate attorney P/61AL2720/ US, Title: "Pellets Containing Plant Extracts, Process of Making Same and Their Pharmaceutical Peroral or Cosmetic Use", U.S. Ser No. 07/876,866.

File No. of the German associate attorney P/61AL2721/ US, Title: "Soft Gelatin Capsules", U.S. Ser. No. 07/876, 863.

File No. of the German associate attorney P/61AL2723/ US, Title: "Pellets Containing Dihydropyridine Derivatives Process for Production Thereof and Use as Rapid Action Dosage in Heart and Circulatory Diseases", U.S. Ser. No. 07/876,877.

Peptide pharmaceuticals in particular insulin may, in accordance with the processes described in the above identified patent applications, be brought into a perorally acceptable dosage form.

Insulin is a peptide pharmaceutical which consists of 51 amino acids which are oriented in two chains (a- and b-chain). Insulin is exceedingly sensitive to external influences. Such influences include heat and alkali sensitivity, sensitivity with respect to oxidizing and reducing agents, as well as to strong acidly reacting substances. Because of its isoelectric point (IEP) of 5.3 to 5.4, insulin is soluble in weakly acid environments of pH 3 to 4, as well as in weak acid environments at pH 7 to 8, as well as being adequately stable. In the indicated pH ranges, the molecule may be positive (pH<IEP) or negatively charged where the pH is greater than the IEP.

In a particular embodiment of the present invention which is claimed in the subclaims, peptide pharmaceuticals in particular insulin, are provided in a form in which the peptide pharmaceutical, in charged and at the same time dissolved form, is associated with a contrary-wise charged gelatin or gelatin derivative, through absorptive charge compensation (pseudo coaszervate).

In the acid range below pH 5.3 to 5.4, wherein the insulin molecule is positively charged, there may only be utilized negatively charged gelatins. Other than type B gelatin, there may also be considered certain molar fractions of this gelatin, so-called fractionated gelatins, as well as gelatin derivatives in particular succinylated gelatin. These show, in the foregoing pH range, the same behavior as type B gelatin. The only type B gelatin which is suitable is one which has an isoelectric point of less than 5.3 to 5.4 and thus, at ph values above its IEP, is negatively charged. On the other hand, at a pH value of greater than 5.3 to 5.4, insulin is negatively charged. This negative charge can analogously only be compensated by type A gelatin, which carries a positive charge at a pH value greater than 5.3–5.4, up to pH about 9.5. Commercially available gelatins of type A have an isoelectric point in the region of 6.3 to about 9.5.

In a dosage form in accordance to this principal, type A gelatin is particularly desired. The reason is that surprisingly the following has been found:

After reaching the small intestine or colon, wherein physiological pH values of about 6 to 7.5 predominate and the insulin release from the dosage form begins, the encompassing gelatin particles protect the insulin molecule most effectively from enzymatic degradation by peptidases.

Therein, an additional effect of the gelatin is advantageously noted. The high molecular segments of the gelatin (preferred from a molecular weight range of about $10^7$D, create a spherically formed networks. These networks additionally inhibit the diffusion of the degrading enzyme so that the insulin molecule is even better protected. On the other hand, these gelatin particles or networks show a good adhesion to the upper surfaces of the mucosa which ensures the optimal conditions for absorption. By shifting the pH to pH values higher than 6, insulin is no longer positively charged but rather countercharged and can thus be released from the "complex" (pseudocoaszervate) with gelatin whose charge moves even further into the negative region. It is the finding of the present invention that this "charge change process" can additionally be accelerated by the presence of a buffer substance, i.e., disodium hydrogen phosphate (whose maximum buffer capacity lies at pH values greater than 6) in the gelatin matrix. It is however necessary to stress, that one is not here concerned with a genuine chelation complex as occurs, for example, with cyclodextrins. The insulin liberation in any event proceeds without the conventional precharged equilibrium of the cyclodextrine combination. This provides the optimal conditions for insulin absorption in the gastrointestinal tract.

In order to effectively employ this principle for a peroral dosage form of insulin as well as for other medicaments, even more effectively, the above identified dosage form can be produced suitably in a sandwich tablet or even better, a coated tablet. Suitably, the tablet is coated with an appropriate film coating such as Eudragit Registered Trademark (ROEHM Pharma, Germany) which is gastric juice resistant. It is particularly desirable to use Uudragit S, mixtures of Eudragit S and Eudragit RS types or mixtures of Eudragit S, Eudragit L and Eudragit RS types. These film coatings have the advantage that until solution, they are water impermeable and only begin to dissolve at pH's of about 7, that is to say, when the dosage form is already in the lower section of the intestine, or already in the colon. At this point in time, the dosage form and the active material contained therein (insulin) is additionally well protected from enzymatic degradationby the enzymes of the digestive fluid.

The first layer, that is to say, the coating on the dosage form, is now so constructed that a relatively slow (retarded) release of active material occurs within about 4 hours. The second layer however, that is to say, the core of the coated tablet, is so constructed that a rapid (nonretarded) release of the active material occurs. This combination of acute and retarded form in a single tablet has the advantage that the rapid insulin release in any event, only occurs after reaching the colon, which is known to be medium having a low level of peptidase.

This ensures a continuing provision of the organism with insulin so that a matching of the patient's insulin need to food intake may be readily achieved. In accordance with this invention therefore, it is possible to obtain in this manner, an independence from insulin injection and the patient compliance is therefore considerably higher.

In addition to insulin, wherein it is understood to mean regular insulin, zinc-complexed insulin or globulin-zinc-insulin, other peptide medicaments may be utilized in the present invention which are enzymatically inactivated in the gastrointestinal tract. Among these may be mentioned octreocid, desmopressin, vasopressin, tritorelin, body generated peptide hormones such as gonadotropin, releasing hormone, somatotropin releasing hormone, corticotropin releasing hormone or thyrotropin releasing hormone, polypeptide antibiotics, cyclosporin, buserelin, calcitonin, gonadorelin, lysoprenon, oxytocin, protirelin, hirodin, glucagon, encephalin or adrenocortotropic hormone. Materials for the treatment of ainsporin (renin antagonists), the treatment of hypertension (renin antagonists, enalapril, captopril), antibiotics, which are derived from amino acids, penicillins, (ampicillin), cephalosporin (cephaloxin), carbapenems, (thienamycin) interferons (alpha-interferon) and vaccines. The present invention also suggests a simple process for the formation of the previously described dosage forms.

It is preferred to select a high viscosity gelatin with corresponding bloom value (about 200–300 bloom, with a maximum molecular weight distribution in the range of 9.5 to $10^6$. It is preferred to utilize type B with an IEP in the range of 3.5 to about 5.3, which is totally free of extraneous ions.

As the gelatins which are utilized for retarding layer, for example the coating of the dosage form in accordance with the present invention, there are utilized materials which are converted into the sol form at temperature which is above 37° C. yet under the temperature at which the insulin is already "inactivated" with water. The gelatin concentrations generally lie in the range of 0.1 to 20% (wt/wt), preferably however between 0.5 and 5%. The pH of the sol is adjusted by the addition of acid or base to a value which lies above that of the IEP of the gelatin selected and below the IEP of the insulin charged. This ensures that the gelatin molecules carry sufficient negative charge in order to activate the absorptive charge compensation (pseudocoaszervate) with the insulin molecule. The insulin, for example 50–500 I.U. can be charged directly to the gelatin sol and dissolved therein by stirring. Alternatively, it may be added to the gelatin sol already in dissolved form. The thus achieved charge compensation (pseudocoaszervate formation) can for example be followed by a simple conductivity measurement of the system. It can be advantageous that the pH of the system is postadjusted to the above identified value if this shifts during the process.

The water may now be removed by conventional means, that is to say, by spray or freeze drying, wherein the desired condition of the system is locked in the dried form.

Analogous thereto, it is possible to produce a second dry system which lays the groundwork for a second layer, that is to say, the formation of a core according to the dosage form of the present invention. In this case, there are employed gelatins of the same type and identical IEP, which have a maximum molecular weight distribution below $10^5$, so that a non-retarded release may be obtained (about 30 to about 80 bloom or collagen hydrolysate).

The dried powders can be compounded with the usual inactive ingredients as for example fillers (for example spray dried lactose); buffers (for example disodium citrate), flow regulators (for example highly dispersed silicon dioxide), lubricants (for example magnesium stearate), mold separation materials (for example stearic acid), on suitable tableting presses to form conventional tablets, sandwich, or coated tablets. Surprisingly, the tablets of the present invention have a very high breaking resistance (greater than 50 Newtons) and a lower friability (under 1%). The typical content of inactive ingredients is between 0.1 to 30% relative to the powder to be utilized.

Also the adsorption accelerators (enhancers) disclosed in the copending, cofiled patent application entitled Pellets Containing Peptides, Method of Making Same and Use Thereof, carrying German Attorney's file number P/61AL2718/US, U.S. Ser. No. 07/876,865, now abandoned can be added in quantities of between 0.1% to 10%.

The layer of the sandwich tablet which should not act as a retarded release, can be separately produced and coated in advance with one of the aforementioned film forming agents.

Subsequently, the tablets of the present invention, produced by the present invention, i.e., regular tablet, sandwich tablets and coated tablets, can be coated with film forming agents in the usual manner, for example, by vortexing in a appropriate vessel such as a coating pan. It is particularly advantageous to utilize Eudragit S or mixtures of Eudragit D with Eudragit RS, for example, in a mixture relationship of 3:2.

Both of the herein described systems for the retarded and nonretarded insulin can, via the appropriate granulation methods, also be made into granulated, that is to say, classical pellets. Such granulates or pellets can for example be charged to hard gelatin capsules. Granulates, pellets, and hard gelatin capsules are coated with the same film formers as are used in the tablets of the present invention, in order achieve at least a gastric juice resistance. In a similar manner, there may be produced rapid and delayed release pellets in a single dosage form (hard gelatin capsules) wherein the pellet types are additionally coated with different types of film forming agents. This thus enables the matching of the insulin need of the organism in a more exact manner than is already possible by utilizing the tablet form.

Peroral pellet dosage forms further characterize themselves in that their gastrointestinal transit time is substantially more independent of physiological influence factors, for example, the time and amount of absorbed foodstuffs than are, for example, single unit dosage forms as for example, tablets.

In the present patent application, the peroral dosage forms may be advantageously utilized for other modes of application.

Thus, for example, a tablet formed in accordance with the present invention, in particular, a simple delayed release preparation, may be utilized for the dosing of peptide pharmaceuticals in the oral cavity (Buccal or sublingual). The bioadhesive properties of gelatin serve to adhere to the oral mucosa after contact with physiological fluids.

In accordance with the present invention, spray or freeze-dried powders may be formulated in nasal sprays or nasal gels (nasal application). After dusting into the nasal cavity, the gelatin/pharmaceutical particles, because of the bioadhesive properties of the nasal mucosa and have a transit time of between 3 to 4 hours in the nose.

The following examples are set forth in order to illustrate the invention but are in no way considered to limit the scope thereof.

EXAMPLE 1

Active substance—Normal Insulin (DAB)—9
Gelatin: Type B, totally free of foreign ions.
IEP:—3.5
bloom No. 280 for Delayed release—30 for Rapid Release.

To 500 g. of the above specified gelatin there is added sufficient water at 40° C. to convert the same into a sol form in a 5% solution. The pH of said sol is adjusted to 3.9. Thereafter, into each portion there are added 30,000 IU of insulin of the indicated specification. The thus produced adsorptive loading compensation (pseudocoaszervate formation) is followed by the conductivity determination (for example with a microprocessor controlled high efficiency conductometer produced by the WYT Company), until no further change in the total conductivity occurs.

Thereafter, both solutions are dried by spray drying at a exit temperature of the spray stream of about 45–50° C. to provide the dry form.

By the addition of conventional pharmaceutical inactive ingredients, there are produced coated tablets on a tablet press (average press pressure 10 kN) which contain in their core, insulin in non-retarded form. The tablet precursors are then coated by spraying in a coating pan with a mixture of Eudragit S and Eudragit RS in the ratio of 3:2 in acetone (5% solution).

EXAMPLE 2

Analogous to Example 1, a dried powder is produced. Together with the addition of the usual pharmaceutical inactive ingredients, the powder is granulated and formed into pellets (Vortex coating granulator). Thereafter the pellets to be utilized for quick insulin release are coated in the coating pan with an acetone solution spray of Eudragit S and Eudragit RS in the ratio of 3:2, the pellets to be used for retarded insulin liberation and are analogously coated with Eudragit S (both in 5% acetone solution).

Both pellet sorts, in the ratio of 1:1 are then charged to hard gelatin capsules which, after closing, are coated with Eudragit S.

EXAMPLE 3

Corticotropin, IEP in weak alkali range, about 8
Gelatin type A—totally free of foreign ions—IEP-9.0
bloom No. 320 for retarded release—30 for rapid release
300 g. portions of the above specified gelatins are converted with distilled water at 40° C. in a sol form so that a 3% solution thereof is formed. Utilizing 2% aqueous hydrochloric acid, the respective sols are brought to a pH value of 8.5. Thereafter, each portion has dissolved therein 200 mg of corticotropin.

Thereafter, each solution is separately spray dried at an exit temperature of the spray stream of about 45–50° C. to produce a dry form.

Utilizing conventional pharmaceutical inactive ingredients, coated tablets are formed on a tableting press whose core comprise s the corticotropin in non-retardant form. The tablet precursors are then coated in a cosating pan by spraying with a 5% acetone solution of Eudragit S.

What is claimed is:

1. Dry pellets containing peptide pharmaceuticals, in oral, buccal, sublingual or nasally administrable dosage form comprising at least one peptide pharmaceutical having a given net charge dispersed in a matrix which comprises
   a member seldBted from the froup consisting of gelatin, fractionated gelatins, collagen hydrolysates, crosslinked gelatins and mixtures thereof,
   said member or members of said group of hydrophilic molecules carrying a sufficient contrary net charge to form a psuedocoazervate with said peptide pharmaceutical.

2. Dry pellets of claim 1 wherein said peptide is dispersed in a matrix whose component molecules are insoluble in aqueous media below 37° C.

3. Dry pellets of claim 1 wherein said peptide pharmaceutical is insulin.

4. Dry pellets of claim 1 wherein the major portion of the gelatin has a molecular weight distribution between $9 \times 10^4$ and $10^7$ D.

5. Dry pellets of claim 1 wherein said peptide pharmaceutical is substantially microencapsulated in gelatin.

6. Peroral dosage form for a peptide pharmaceutical in accordance with claim 2, wherein the gelatin has a bloom value of between 30 and 320, the fractioned gelatins, when present, have a molecular weight exceeding $9.5 \times 10^4$ D, and the cllagen hydrolysates, when present, have a molecular weight between 100 and $9.5 \times 10^4$ D.

7. Dry pellets of claim 1 having a synthetic or natural coating.

8. Peroral dosage form for a peptide pharmaceutical wherein the dry pellets of claim 7 are provided as coated tablets.

9. Peroral dosage form for a peptide pharmaceutical of claim 7 wherein slow dissolving forms are combided with rapid dissolving forms.

10. Peroral dosage form for a peptide pharmaceutical in accordance with claim 9 in tablet form, having a first, outward-most coated layer in delayed release form and a second coated layer in rapid release form.

* * * * *